United States Patent [19]

Feitelson

[11] Patent Number: 5,670,365

[45] Date of Patent: Sep. 23, 1997

[54] IDENTIFICATION OF, AND USES FOR, NEMATICIDAL BACILLUS THURINGIENSIS GENES, TOXINS, AND ISOLATES

[75] Inventor: Jerald S. Feitelson, San Diego, Calif.

[73] Assignee: Mycogen Corporation, San Diego, Calif.

[21] Appl. No.: 620,717

[22] Filed: Mar. 21, 1996

Related U.S. Application Data

[63] Continuation-in-part of Ser. No. 540,104, Oct. 6, 1995.

[51] Int. Cl.[6] .................... C12N 1/20; C12N 15/00; C07H 21/04; A01N 37/18
[52] U.S. Cl. .................. 435/252.3; 435/252.31; 435/252.33; 536/23.7; 536/24.32; 536/24.33; 536/23.71; 514/2; 930/200; 935/8; 935/9; 935/10; 935/66
[58] Field of Search ................. 435/252.3, 252.31, 435/270, 832, 252.33; 536/23.7, 24.32, 24.33, 23.71; 514/2; 930/200; 935/9, 10, 8, 66, 72, 73

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,797,276 | 1/1989 | Herrnstadt et al. | 424/84 |
| 4,853,331 | 8/1989 | Herrnstadt et al. | 435/252.3 |
| 4,918,006 | 4/1990 | Ellar et al. | 435/69.1 |
| 4,948,734 | 8/1990 | Edwards et al. | 514/2 |
| 4,990,332 | 2/1991 | Payne et al. | 424/93.461 |
| 5,039,523 | 8/1991 | Payne et al. | 424/93.461 |
| 5,093,120 | 3/1992 | Edwards et al. | 514/2 |
| 5,126,133 | 6/1992 | Payne et al. | 424/93.461 |
| 5,151,363 | 9/1992 | Payne | 435/252.5 |
| 5,164,180 | 11/1992 | Payne et al. | 424/93.461 |
| 5,169,629 | 12/1992 | Payne et al. | 424/93.461 |
| 5,204,237 | 4/1993 | Gaertner et al. | 435/6 |
| 5,236,843 | 8/1993 | Narva et al. | 435/252.3 |
| 5,262,399 | 11/1993 | Hickle et al. | 424/93.2 |
| 5,270,448 | 12/1993 | Payne | 514/2 |
| 5,281,530 | 1/1994 | Sick et al. | 435/252.3 |
| 5,322,932 | 6/1994 | Narva et al. | 530/350 |
| 5,350,577 | 9/1994 | Payne | 424/93.461 |
| 5,426,049 | 6/1995 | Sick et al. | 435/252.3 |
| 5,439,881 | 8/1995 | Narva et al. | 514/2 |
| 5,527,883 | 6/1996 | Thompson et al. | 530/350 |
| 5,554,534 | 9/1996 | Michaels et al. | 435/252.3 |
| 5,589,382 | 12/1996 | Payne et al. | 435/252.5 |
| 5,596,071 | 1/1997 | Payne et al. | 530/350 |
| 5,602,032 | 2/1997 | Liu et al. | 435/252.31 |

FOREIGN PATENT DOCUMENTS

| | | |
|---|---|---|
| 9416079 | 3/1991 | WIPO. |
| 9220802 | 11/1992 | WIPO. |

OTHER PUBLICATIONS

Metcalf, R.L. (1986) "Methods for the Study of Pest *Diabrotica*", pp. xii–xv.

Schnepf, H.E., H.R. Whiteley (1981) "Cloning and expression of the *Bacillus thuringiensis* crystal protein gene in *Escherichia coli*" Proc. Natl. Acad. Sci. USA 78(5):2893–2897.

Feitelson, J.S. et al. (1992) "*Bacillus thuringiensis*: Insects and Beyond" Bio/Technology 10:271–275.

Hofte, H., H.R. Whiteley (1989) "Insecticidal Crystal Proteins of *Bacillus thuringiensis*" Microbiological Reviews 53(2):242–255.

Kreig, V.A. et al. (1983) "*Bacillus thuringiensis* var. *tenebrionis*: ein neuer, gegenuber Larven von Colepteren wirksamer Pathotyp" Z. ang. Ent. 96:500–508.

Beegle, C.C. (1978) "Use of Entomogenous Bacteria in Agroecosystems" Developments in Industrial Microbiology 20:97–104.

Couch, T.L. (1980) "Mosquito Pathogenicity of *Bacillus thuringiensis* var. *israelensis*" Developments in Industrial Microbiology 22:61–67.

Gaertner, F. (1990) "Cellular delivery systems for insecticidal proteins: living and non–living microorganisms" Controlled Delivery of Crop–Protection Agents, pp. 245–257.

Gaertner, F., L. Kim (1988) "Current Applied Recombinant DNA Projects" TIBTECH 6:S4–S7.

Bottjer, K.P. et al. (1985) "Nematoda: Susceptibility of the Egg to *Bacillus thuringiensis* Toxins" Experimental Parasitology 60:239–244.

Ignoffo, C.M., V.H. Dropkin (1977) "Deleterious Effects of the Thermostable Toxin of *Bacillus thuringiensis* on Species of Soil–Inhabiting, Myceliophagus, and Plant–Parasitic Nematodes" Journal of the Kansas Entomological Society 50(3):394–398.

Ciordia, H., W.E. Bizzell (1961) "A Preliminary Report on the Effects of *Bacillus thuringiensis* var. *thuringiensis* Berliner on the Development of the Free–Living Stages of Some Cattle Nematodes" Journal of Parasitology 47:41, *abstract No. 86.

Coles, G.C. (1986) "Anthelmintic Resistance in Sheep" Veterinary Clinics of North American, Food Animal Practice 2(2):423–432.

Prichard, R.K. et al. (1980) "The Problem of Anthelmintic Resistance in Nematodes" Australian Veterinary Journal 56:239–251.

Carozzi, N.B. et al. (1991) "Prediction of Insecticidal Activity of *Bacillus thuringiensis* Strains by Polymerase Chain Reaction Product Profiles" Applied and Environmental Microbiology 57(11):3057–3061.

*Primary Examiner*—Bradley L. Sisson
*Attorney, Agent, or Firm*—Saliwanchik, Lloyd & Saliwanchik

[57] ABSTRACT

Disclosed and claimed are novel nucleotide primers for the identification of genes encoding toxins active against nematodes and coleopterans. The primers are useful in PCR techniques to produce gene fragments which are characteristic of genes encoding these toxins. The primers are also useful as nucleotide probes to detect the toxins-encoding genes. The subject invention also concerns novel isolates, toxins, and genes useful in the control of plant pests.

23 Claims, No Drawings

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:1:

GATCGTMTWG ARTTTRTTCC    20

( 2 ) INFORMATION FOR SEQ ID NO:2:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

AAAGTNGATG CMTTATCWGA TGA         23

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

ACACGTTATA HDGTTTCTGG         20

( 2 ) INFORMATION FOR SEQ ID NO:4:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

TCATCWGATA AKGCATCNAC         20

( 2 ) INFORMATION FOR SEQ ID NO:5:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

TGGACGDTCT TCAMKAATTT CYAAA         25

( 2 ) INFORMATION FOR SEQ ID NO:6:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

CCGGAGGAAG GTGGGGATG         19

( 2 ) INFORMATION FOR SEQ ID NO:7:

( i ) SEQUENCE CHARACTERISTICS:

(A) LENGTH: 17 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:7:

CGATTACTAG CGATTCC 17

(2) INFORMATION FOR SEQ ID NO:8:

(i) SEQUENCE CHARACTERISTICS:
(A) LENGTH: 3504 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 167P (xi) SEQUENCE DESCRIPTION: SEQ ID NO:8:

| | | | | | | |
|---|---|---|---|---|---|---|
| ATGACAAATC | CAACTATACT | ATATCCTAGT | TACCATAATG | TATTAGCTCA | TCCGATTAGA | 60 |
| TTAGATTCTT | TTTTGATCC | ATTTGTAGAG | ACATTTAAGG | ATTTAAAAGG | GGCTTGGGAA | 120 |
| GAATTCGGAA | AAACGGGATA | TATGGACCCC | TTAAAACAAC | ACCTTCAAAT | CGCATGGGAT | 180 |
| ACTAGTCAAA | ATGGAACAGT | GGATTATTTA | GCATTAACAA | AAGCATCTAT | ATCTCTCATA | 240 |
| GGTTTAATTC | CTGGTGCAGA | CGCTGTAGTC | CCTTTTATTA | ATATGTTTGT | AGACTTTATT | 300 |
| TTTCCGAAAT | TATTTGGAAG | AGGTTCTCAA | CAAATGCTC | AAGCTCAATT | TTTCGAACTA | 360 |
| ATCATAGAAA | AAGTTAAAGA | ACTTGTTGAT | GAAGATTTTA | GAAACTTTAC | CCTTAATAAT | 420 |
| CTACTCAATT | ACCTTGATGG | TATGCAAACA | GCCTTATCAC | ATTTCCAAAA | CGATGTACAA | 480 |
| ATTGCTATTT | GTCAAGGAGA | ACAACCAGGA | CTTATGCTAG | ATCAAACACC | AACGGCTTGT | 540 |
| ACTCCTACTA | CAGACCATTT | AATTTCTGTA | AGAGAATCTT | TTAAAGATGC | TCGAACTACA | 600 |
| ATTGAAACAG | CTTTACCACA | TTTTAAAAAT | CCTATGCTAT | CCACAAATGA | TAACACTCCA | 660 |
| GATTTTAATA | GCGACACTGT | CTTATTAACA | TTACCAATGT | ATACAACAGC | AGCGACTTTA | 720 |
| AATCTTATAT | TACATCAAGG | GTATATTCAA | TTCGCAGAAA | GATGGAAATC | TGTAAATTAT | 780 |
| GATGAAAGTT | TTATAAATCA | AACAAAAGTT | GATTTGCAAC | GTCGTATTCA | GGACTATTCT | 840 |
| ACTACTGTAT | CTACCACTTT | TGAAAAATTC | AAACCTACTC | TAAATCCATC | AAATAAGAA | 900 |
| TCTGTTAATA | AGTATAATAG | ATATGTTCGT | TCCATGACTC | TTCAATCTTT | AGACATTGCT | 960 |
| GCAACATGGC | CTACTTTAGA | TAATGTTAAT | TACCCTTCCA | ATGTAGATAT | TCAATTGGAT | 1020 |
| CAAACTCGCT | TAGTATTTTC | AGATGTTGCA | GGACCTTGGG | AAGGTAATGA | TAATATAACT | 1080 |
| TCGAATATTA | TAGATGTATT | AACACCAATA | AATACAGGGA | TAGGATTTCA | AGAAAGTTCA | 1140 |
| GATCTTAGAA | AATTCACTTA | TCCACGAATA | GAATTACAAA | GCATGCAATT | CCATGGACAA | 1200 |
| TATGTAAACT | CAAAAGTGT | AGAACATTGT | TATAGCGATG | GTCTTAAATT | AAATTATAAA | 1260 |
| AATAAAACTA | TAACTGCAGG | TGTAAGTAAT | ATTGATGAAA | GTAATCAAAA | TAATAAACAT | 1320 |
| AACTATGGTC | CTGTAATAAA | TAGTCCTATT | ACTGATATCA | ACGTAAATTC | CCAAAATTCT | 1380 |
| CAATATTTAG | ATTTAAATTC | AGTCATGGTA | AATGGTGGTC | AAAAAGTAGC | CGGGTGTTCA | 1440 |
| CCACTTAGTT | CAAATGGTAA | TTCTAATAAT | GCTGCTTTAC | CTAATCAAAA | AATAAATGTT | 1500 |
| ATTTATTCAG | TACAATCAAA | TGATAAACCA | GAAAACATG | CAGACACTTA | TAGAAAATGG | 1560 |
| GGATATATGA | GCAGTCATAT | TCCTTATGAT | CTTGTTCCAG | AAAATGTAAT | TGGAGATATA | 1620 |

```
GATCCGGATA CTAAACAACC GTCATTGCTT CTTAAAGGGT TTCCGGCAGA AAAAGGATAT      1680

GGTGACTCAA TTGCATATGT ATCAGAACCT TTAAATGGTG CGAATGCAGT TAAACTTACT      1740

TCATATCAAG TTCTCAAAAT GGAAGTTACA AATCAAACAA CTCAAAATA TCGTATTCGC       1800

ATACGTTATG CTACAGGTGG AGATACAGCT GCTTCTATAT GGTTTCATAT TATTGGTCCA      1860

TCTGGAAATG ATTTAACAAA CGAAGGCCAT AACTTCTCTA GTGTATCTTC TAGAAATAAA      1920

ATGTTTGTTC AGGGTAATAA CGGAAAATAT GTATTGAACA TCCTTACAGA TTCAATAGAA      1980

TTACCATCAG GACAACAAAC TATTCTTATT CAAATACTA ATTCTCAAGA TCTTTTTTA       2040

GATCGTATTG AATTTATTTC TCTCCCTTCT ACTTCTACTC CTACTTCTAC TAATTTTGTA      2100

GAACCTGAAT CATTAGAAAA GATCATAAAC CAAGTAATC AATTATTTAG CTCCTCATCT      2160

CAAACTGAAT TGGCTCACAC TGTAAGCGAT TATAAAATTG ATCAAGTAGT GCTAAAAGTA      2220

AATGCCTTAT CCGACGATGT ATTTGGTGTA GAGAAAAAAG CATTACGTAA ACTTGTGAAT      2280

CAGGCCAAAC AACTCAGTAA AGCACGAAAT GTATTGGTCG GTGGAAACTT TGAAAAAGGT      2340

CATGAATGGG CACTAAGCCG TGAAGCAACA ATGGTCGCAA ATCATGAGTT ATTCAAAGGG      2400

GATCATTTAT TATTACCACC ACCAACCCTA TATCCATCGT ATGCATATCA AAAAATTGAT      2460

GAATCGAAAT TAAAATCCAA TACACGTTAT ACTGTTTCCG GCTTATTGC GCAAAGTGAA       2520

CATCTAGAAG TCGTTGTGTC TCGATACGGG AAAGAAGTAC ATGACATGTT AGATATCCCG      2580

TATGAAGAAG CCTTACCAAT TTCTTCTGAT GAGAGTCCAA ATTGTTGCAA ACCAGCTGCT      2640

TGTCAGTGTT CATCTTGTGA TGGTAGTCAA TCAGATTCTC ATTTCTTTAG CTATAGTATC      2700

GATGTTGGTT CCCTACAATC AGATGTAAAT CTCGGCATTG AATTCGGTCT TCGTATTGCG      2760

AAACCAAACG GATTTGCGAA AATCAGTAAT CTAGAAATTA AGAAGATCG TCCATTAACA       2820

GAAAAGAAA TCAAAAAAGT ACAACGTAAA GAACAAAAAT GGAAAAAGC ATTTAACCAA        2880

GAACAAGCCG AAGTAGCGAC AACACTCCAA CCAACGTTAG ATCAAATCAA TGCTTTGTAT      2940

CAAAATGAAG ATTGGAACGG TTCCGTTCAC CCGCATGTGA CCTATCAACA TCTGTCCGCT      3000

GTTGTTGTAC CAACGTTACC AAAACAAAGA CATTGGTTTA TGGAGGATCG AGAAGGCGAA      3060

CATGTTGTTC TGACGCAACA ATTCCAACAA GCATTGGATC GTGCGTTCCA ACAAATCGAA      3120

GAACAAAACT TAATCCACAA TGGTAATTTT GCGAATGGAT TAACAGATTG GACTGTCACA      3180

GGAGATGCAC AACTTACGAT CTTTGACGAA GATCCAGTAT TAGAACTAGC GCATTGGGAT      3240

GCAAGTATCT CTCAAACCAT TGAAATTATG GATTTGAAG AAGACACAGA ATACAAACTG       3300

CGTGTACGTG GAAAAGGCAA AGGAACAGTT ACCGTTCAAC ATGGAGAAGA AGAATTAGAA      3360

ACGATGACAT TCAATACAAC GAGTTTTACA ACACAAGAAC AAACCTTCTA CTTCGAAGGA      3420

GATACAGTGG ACGTACATGT TCAATCAGAG AATAACACAT TCCTGATAGA TAGTGTGGAA      3480

CTCATTGAAA TCATAGAAGA GTAA                                              3504
```

( 2 ) INFORMATION FOR SEQ ID NO:9:

( i ) SEQUENCE CHARACTERISTICS:
( A ) LENGTH: 1168 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( C ) INDIVIDUAL ISOLATE: 167p ( x i ) SEQUENCE DESCRIPTION: SEQ ID NO:9:

-continued

| | | | | | | | | | | | | | | |
|---|---|---|---|---|---|---|---|---|---|---|---|---|---|---|
| Met 1 | Thr | Asn | Pro | Thr 5 | Ile | Leu | Tyr | Pro | Ser 10 | Tyr | His | Asn | Val | Leu Ala 15 |
| His | Pro | Ile | Arg 20 | Leu | Asp | Ser | Phe | Phe 25 | Asp | Pro | Phe | Val | Glu 30 | Thr Phe |
| Lys | Asp | Leu 35 | Lys | Gly | Ala | Trp | Glu 40 | Glu | Phe | Gly | Lys | Thr 45 | Gly | Tyr Met |
| Asp | Pro 50 | Leu | Lys | Gln | His | Leu 55 | Gln | Ile | Ala | Trp | Asp 60 | Thr | Ser | Gln Asn |
| Gly 65 | Thr | Val | Asp | Tyr | Leu 70 | Ala | Leu | Thr | Lys | Ala 75 | Ser | Ile | Ser | Leu Ile 80 |
| Gly | Leu | Ile | Pro | Gly 85 | Ala | Asp | Ala | Val | Val 90 | Pro | Phe | Ile | Asn | Met Phe 95 |
| Val | Asp | Phe | Ile 100 | Phe | Pro | Lys | Leu | Phe 105 | Gly | Arg | Gly | Ser | Gln 110 | Gln Asn |
| Ala | Gln | Ala 115 | Gln | Phe | Phe | Glu | Leu 120 | Ile | Ile | Glu | Lys | Val 125 | Lys | Glu Leu |
| Val | Asp 130 | Glu | Asp | Phe | Arg | Asn 135 | Phe | Thr | Leu | Asn | Asn 140 | Leu | Leu | Asn Tyr |
| Leu 145 | Asp | Gly | Met | Gln | Thr 150 | Ala | Leu | Ser | His | Phe 155 | Gln | Asn | Asp | Val Gln 160 |
| Ile | Ala | Ile | Cys | Gln 165 | Gly | Glu | Gln | Pro | Gly 170 | Leu | Met | Leu | Asp | Gln Thr 175 |
| Pro | Thr | Ala | Cys 180 | Thr | Pro | Thr | Thr | Asp 185 | His | Leu | Ile | Ser | Val 190 | Arg Glu |
| Ser | Phe | Lys 195 | Asp | Ala | Arg | Thr | Thr 200 | Ile | Glu | Thr | Ala | Leu 205 | Pro | His Phe |
| Lys | Asn 210 | Pro | Met | Leu | Ser | Thr 215 | Asn | Asp | Asn | Thr | Pro 220 | Asp | Phe | Asn Ser |
| Asp 225 | Thr | Val | Leu | Leu | Thr 230 | Leu | Pro | Met | Tyr | Thr 235 | Thr | Ala | Ala | Thr Leu 240 |
| Asn | Leu | Ile | Leu | His 245 | Gln | Gly | Tyr | Ile | Gln 250 | Phe | Ala | Glu | Arg | Trp Lys 255 |
| Ser | Val | Asn | Tyr 260 | Asp | Glu | Ser | Phe | Ile 265 | Asn | Gln | Thr | Lys | Val 270 | Asp Leu |
| Gln | Arg | Arg 275 | Ile | Gln | Asp | Tyr | Ser 280 | Thr | Thr | Val | Ser | Thr 285 | Thr | Phe Glu |
| Lys | Phe 290 | Lys | Pro | Thr | Leu | Asn 295 | Pro | Ser | Asn | Lys | Glu 300 | Ser | Val | Asn Lys |
| Tyr 305 | Asn | Arg | Tyr | Val | Arg 310 | Ser | Met | Thr | Leu | Gln 315 | Ser | Leu | Asp | Ile Ala 320 |
| Ala | Thr | Trp | Pro | Thr 325 | Leu | Asp | Asn | Val | Asn 330 | Tyr | Pro | Ser | Asn | Val Asp 335 |
| Ile | Gln | Leu | Asp 340 | Gln | Thr | Arg | Leu | Val 345 | Phe | Ser | Asp | Val | Ala 350 | Gly Pro |
| Trp | Glu | Gly 355 | Asn | Asp | Asn | Ile | Thr 360 | Ser | Asn | Ile | Ile | Asp 365 | Val | Leu Thr |
| Pro | Ile 370 | Asn | Thr | Gly | Ile | Gly 375 | Phe | Gln | Glu | Ser | Ser 380 | Asp | Leu | Arg Lys |
| Phe 385 | Thr | Tyr | Pro | Arg | Ile 390 | Glu | Leu | Gln | Ser | Met 395 | Gln | Phe | His | Gly Gln 400 |
| Tyr | Val | Asn | Ser | Lys 405 | Ser | Val | Glu | His | Cys 410 | Tyr | Ser | Asp | Gly | Leu Lys 415 |
| Leu | Asn | Tyr | Lys | Asn | Lys | Thr | Ile | Thr | Ala | Gly | Val | Ser | Asn | Ile Asp |

-continued

```
              420                    425                      430
Glu  Ser  Asn  Gln  Asn  Asn  Lys  His  Asn  Tyr  Gly  Pro  Val  Ile  Asn  Ser
               435                    440                    445
Pro  Ile  Thr  Asp  Ile  Asn  Val  Asn  Ser  Gln  Asn  Ser  Gln  Tyr  Leu  Asp
     450                    455                    460
Leu  Asn  Ser  Val  Met  Val  Asn  Gly  Gly  Gln  Lys  Val  Ala  Gly  Cys  Ser
465                      470                    475                       480
Pro  Leu  Ser  Ser  Asn  Gly  Asn  Ser  Asn  Asn  Ala  Ala  Leu  Pro  Asn  Gln
                    485                    490                         495
Lys  Ile  Asn  Val  Ile  Tyr  Ser  Val  Gln  Ser  Asn  Asp  Lys  Pro  Glu  Lys
               500                    505                    510
His  Ala  Asp  Thr  Tyr  Arg  Lys  Trp  Gly  Tyr  Met  Ser  Ser  His  Ile  Pro
          515                    520                         525
Tyr  Asp  Leu  Val  Pro  Glu  Asn  Val  Ile  Gly  Asp  Ile  Asp  Pro  Asp  Thr
     530                    535                         540
Lys  Gln  Pro  Ser  Leu  Leu  Leu  Lys  Gly  Phe  Pro  Ala  Glu  Lys  Gly  Tyr
545                      550                    555                       560
Gly  Asp  Ser  Ile  Ala  Tyr  Val  Ser  Glu  Pro  Leu  Asn  Gly  Ala  Asn  Ala
                    565                    570                         575
Val  Lys  Leu  Thr  Ser  Tyr  Gln  Val  Leu  Lys  Met  Glu  Val  Thr  Asn  Gln
               580                    585                    590
Thr  Thr  Gln  Lys  Tyr  Arg  Ile  Arg  Ile  Arg  Tyr  Ala  Thr  Gly  Gly  Asp
          595                    600                    605
Thr  Ala  Ala  Ser  Ile  Trp  Phe  His  Ile  Ile  Gly  Pro  Ser  Gly  Asn  Asp
     610                    615                    620
Leu  Thr  Asn  Glu  Gly  His  Asn  Phe  Ser  Ser  Val  Ser  Ser  Arg  Asn  Lys
625                      630                    635                       640
Met  Phe  Val  Gln  Gly  Asn  Asn  Gly  Lys  Tyr  Val  Leu  Asn  Ile  Leu  Thr
                    645                    650                         655
Asp  Ser  Ile  Glu  Leu  Pro  Ser  Gly  Gln  Gln  Thr  Ile  Leu  Ile  Gln  Asn
               660                    665                    670
Thr  Asn  Ser  Gln  Asp  Leu  Phe  Leu  Asp  Arg  Ile  Glu  Phe  Ile  Ser  Leu
          675                    680                    685
Pro  Ser  Thr  Ser  Thr  Pro  Thr  Ser  Thr  Asn  Phe  Val  Glu  Pro  Glu  Ser
     690                    695                    700
Leu  Glu  Lys  Ile  Ile  Asn  Gln  Val  Asn  Gln  Leu  Phe  Ser  Ser  Ser  Ser
705                      710                    715                       720
Gln  Thr  Glu  Leu  Ala  His  Thr  Val  Ser  Asp  Tyr  Lys  Ile  Asp  Gln  Val
                    725                    730                         735
Val  Leu  Lys  Val  Asn  Ala  Leu  Ser  Asp  Asp  Val  Phe  Gly  Val  Glu  Lys
               740                    745                    750
Lys  Ala  Leu  Arg  Lys  Leu  Val  Asn  Gln  Ala  Lys  Gln  Leu  Ser  Lys  Ala
          755                    760                    765
Arg  Asn  Val  Leu  Val  Gly  Gly  Asn  Phe  Glu  Lys  Gly  His  Glu  Trp  Ala
770                      775                    780
Leu  Ser  Arg  Glu  Ala  Thr  Met  Val  Ala  Asn  His  Glu  Leu  Phe  Lys  Gly
785                      790                    795                       800
Asp  His  Leu  Leu  Leu  Pro  Pro  Thr  Leu  Tyr  Pro  Ser  Tyr  Ala  Tyr
                    805                    810                    815
Gln  Lys  Ile  Asp  Glu  Ser  Lys  Leu  Lys  Ser  Asn  Thr  Arg  Tyr  Thr  Val
               820                    825                    830
Ser  Gly  Phe  Ile  Ala  Gln  Ser  Glu  His  Leu  Glu  Val  Val  Val  Ser  Arg
          835                    840                    845
```

```
Tyr Gly Lys Glu Val His Asp Met Leu Asp Ile Pro Tyr Glu Glu Ala
    850             855             860

Leu Pro Ile Ser Ser Asp Glu Ser Pro Asn Cys Cys Lys Pro Ala Ala
865             870             875             880

Cys Gln Cys Ser Ser Cys Asp Gly Ser Gln Ser Asp Ser His Phe Phe
                885             890             895

Ser Tyr Ser Ile Asp Val Gly Ser Leu Gln Ser Asp Val Asn Leu Gly
            900             905             910

Ile Glu Phe Gly Leu Arg Ile Ala Lys Pro Asn Gly Phe Ala Lys Ile
        915             920             925

Ser Asn Leu Glu Ile Lys Glu Asp Arg Pro Leu Thr Glu Lys Glu Ile
    930             935             940

Lys Lys Val Gln Arg Lys Glu Gln Lys Trp Lys Lys Ala Phe Asn Gln
945             950             955             960

Glu Gln Ala Glu Val Ala Thr Thr Leu Gln Pro Thr Leu Asp Gln Ile
            965             970             975

Asn Ala Leu Tyr Gln Asn Glu Asp Trp Asn Gly Ser Val His Pro His
            980             985             990

Val Thr Tyr Gln His Leu Ser Ala Val Val Val Pro Thr Leu Pro Lys
        995             1000            1005

Gln Arg His Trp Phe Met Glu Asp Arg Glu Gly Glu His Val Val Leu
    1010            1015            1020

Thr Gln Gln Phe Gln Gln Ala Leu Asp Arg Ala Phe Gln Gln Ile Glu
1025            1030            1035            1040

Glu Gln Asn Leu Ile His Asn Gly Asn Phe Ala Asn Gly Leu Thr Asp
            1045            1050            1055

Trp Thr Val Thr Gly Asp Ala Gln Leu Thr Ile Phe Asp Glu Asp Pro
        1060            1065            1070

Val Leu Glu Leu Ala His Trp Asp Ala Ser Ile Ser Gln Thr Ile Glu
    1075            1080            1085

Ile Met Asp Phe Glu Glu Asp Thr Glu Tyr Lys Leu Arg Val Arg Gly
    1090            1095            1100

Lys Gly Lys Gly Thr Val Thr Val Gln His Gly Glu Glu Glu Leu Glu
1105            1110            1115            1120

Thr Met Thr Phe Asn Thr Thr Ser Phe Thr Thr Gln Glu Gln Thr Phe
            1125            1130            1135

Tyr Phe Glu Gly Asp Thr Val Asp Val His Val Gln Ser Glu Asn Asn
            1140            1145            1150

Thr Phe Leu Ile Asp Ser Val Glu Leu Ile Glu Ile Ile Glu Glu Met
        1155            1160            1165
```

IDENTIFICATION OF, AND USES FOR, NEMATICIDAL BACILLUS THURINGIENSIS GENES, TOXINS, AND ISOLATES

CROSS-REFERENCE TO A RELATED APPLICATION

This application is a continuation-in-part of co-pending application Ser. No. 08/540,104, filed Oct. 6, 1995.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner et al., 1988). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *morrisoni* (a.k.a. *tenebrionis*, a.k.a. *B.t.* M-7, a.k.a. *B.t. san diego*), have been used commercially to control insects of the orders Diptera and Coleoptera, respectively (Gaertner, 1989). See also Couch, 1980 and Beegle, 1978. Krieg et al., 1983, describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte and Whiteley, 1989). Höfte and Whiteley classified *B.t.* crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson et al., 1992). CryV has been proposed to designate a class of toxin genes that are nematode-specific.

The cloning and expression of a *B.t.* crystal protein gene in *Escherichia coli* has been described in the published literature (Schnepf and Whiteley, 1981). U.S. Pat. No. 4,448,885 and U.S. Pat. No. 4,467,036 both disclose the expression of *B.t.* crystal protein in *E. coli*. U.S. Pat. Nos. 4,990,332; 5,039,523; 5,126,133; 5,164,180; and 5,169,629 are among those which disclose *B.t.* toxins having activity against lepidopterans. U.S. Pat. Nos. 4,797,276 and 4,853,331 disclose *B. thuringiensis* strain tenebrionis which can be used to control coleopteran pests in various environments. U.S. Pat. No. 4,918,006 discloses *B.t.* toxins having activity against dipterans. U.S. Pat. No. 5,151,363 and U.S. Pat. No. 4,948,734 disclose certain isolates of *B.t.* which have activity against nematodes. Other U.S. patents which disclose activity against nematodes include 5,093,120; 5,236,843; 5,262,399; 5,270,448; 5,281,530; 5,322,932; 5,350,577; 5,426,049; and 5,439,881. As a result of extensive research and investment of resources, other patents have issued for new *B.t.* isolates and new uses of *B.t.* isolates. See Feitelson et al., 1992 for a review. However, the discovery of new *B.t.* isolates and new uses of known *B.t.* isolates remains an empirical, unpredictable art.

Regular use of chemical control of unwanted organisms can select for chemical resistant strains. Chemical resistance occurs in many species of economically important insects and has also occurred in nematodes of sheep, goats, and horses. The development of chemical resistance necessitates a continuing search for new control agents having different modes of action. The subject invention pertains specifically to materials and methods for the identification of *B.t.* toxins active against nematodes or coleopteran pests. Of particular interest among the coleopteran pests is the corn rootworm.

In recent times, the accepted methodology for control of nematodes has centered around the drug benzimidazole and its congeners. The use of these drugs on a wide scale has led to many instances of resistance among nematode populations (Prichard et al., 1980; Coles, 1986). There are more than 100,000 described species of nematodes.

A small number of research articles have been published about the effects of delta endotoxins from *B. thuringiensis* species on the viability of nematode eggs. Bottjer, Bone and Gill, (1985) have reported that *B.t. kurstaki* and *B.t. israelensis* were toxic in vitro to eggs of the nematode *Trichostrongylus colubriformis*. In addition, 28 other *B.t.* strains were tested with widely variable toxicities. Ignoffo and Dropkin, 1977, have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, Ciordia and Bizzell (1961) gave a preliminary report on the effects of *B. thuringiensis* on some cattle nematodes.

There are a number of beetles that cause economic damage. Corn rootworms include species found in the genus Diabrotica (e.g., *D. undecimpunctata undecimpunctata, D. undecimpunctata howardii, D. longicornis, D. virgifera* and *D. balteata*). Corn rootworms cause extensive damage to corn and curcubits. Approximately $250 million worth of insecticides are applied annually to control corn rootworms alone in the United States. Even with insecticide use, rootworms cause about $750 million worth of crop damage each year, making them the most serious corn insect pest in the Midwest.

Current methods for controlling corn rootworm damage in corn are limited to the use of crop rotation and insecticide application. However, economic demands on the utilization of farmland restrict the use of crop rotation. In addition, an emerging two-year diapause (or overwintering) trait of Northern corn rootworms is disrupting crop rotations in some areas.

The use of insecticides to control corn rootworm and other coleopteran pests also has several drawbacks. Continual use of insecticides has allowed resistant insects to evolve. Insecticide use often raises environmental concerns such as contamination of soil and of both surface and underground water supplies. Working with insecticides may also pose hazards to the persons applying them.

At the present time there is a need to have more effective means to control the many nematodes and coleopterans that cause considerable damage to susceptible hosts and crops. Advantageously, such effective means would employ specific biological agents.

*Bacillus thuringiensis* toxins which are active against nematodes and corn rootworm are now known. Isolating responsible toxin genes has been a slow empirical process. Carozzi et al., 1991 describe methods for identifying toxin genes. This report does not disclose or suggest the specific primers and probes of the subject invention for nematode-active and corn rootworm-active toxin genes. U.S. Pat. No. 5,204,237 describes specific and universal probes for the isolation of *B.t.* toxin genes. This patent, however, does not describe the probes and primers of the subject invention.

BRIEF SUMMARY OF THE INVENTION

The subject invention concerns materials and methods useful in the control of pests and, particularly, plant pests. Specifically, the subject invention provides new toxins useful for the control of nematodes. Certain isolates and toxins of the subject invention can also be used to control coleopteran pests, including corn rootworm. The subject invention further provides nucleotide sequences which encode these toxins. The subject invention further provides nucleotide sequences useful in the identification and characterization of genes which encode pesticidal toxins. The subject invention further provides new Bacillus thuringiensis isolates having pesticidal activities.

In one embodiment, the subject invention concerns unique nucleotide sequences which are useful primers in PCR techniques. The primers produce gene fragments which are characteristic of genes encoding nematode-active toxins and, thus, can be used in the identification and isolation of specific toxin genes.

In specific embodiments, the invention concerns the following nucleotide sequences which can be used to identify genes encoding toxins:

1. A forward primer designated V3 whose nucleotide sequence is GATCGTMTWGARTTRTTCC (SEQ ID NO. 1);

2. A forward primer designated V5 whose nucleotide sequence is AAAGTNGATGCMTTATCWGATGA (SEQ ID NO. 2);

3. A forward primer designated V7 whose nucleotide sequence is ACACGTATAHDGTTTFCTGG (SEQ ID NO. 3);

4. A reverse primer designated ΔV5' whose nucleotide sequence is TCATCWGATAAKGCATCNAC (SEQ ID NO. 4); and 5. A reverse primer designated ΔV8' whose nucleotide sequence is TGGACGDTCTTCAMKAATTTCYAAA (SEQ ID NO. 5).

In one embodiment of the subject invention, *B.t.* isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s). In a particularly preferred embodiment, the primer pair V7–ΔV8' is used to identify genes encoding nematicidal *B.t.* toxins.

Another important aspect of the subject invention is the use of the disclosed nucleotide sequences as probes to detect genes encoding *B.t.* toxins which are active against nematodes. The probes may be RNA or DNA. The probe will normally have at least about 10 bases, more usually at least about 18 bases, and may have up to about 50 bases or more, usually not having more than about 200 bases if the probe is made synthetically. However, longer probes can readily be utilized, and such probes can be, for example, several kilobases in length. The probe sequence is designed to be at least substantially complementary to a gene encoding a toxin of interest. The probe need not have perfect complementary to the sequence to which it hybridizes. The probes may be labelled utilizing techniques which are well known to those skilled in this art.

Further aspects of the subject invention include the genes and isolates identified using the methods and nucleotide sequences disclosed herein. The genes thus identified will encode a toxin active against nematodes. Similarly, the isolates will have activity against these pests.

New pesticidal *B.t.* isolates of the subject invention include PS32B, PS49C, PS52E3, PS54G2, PS101CC3, PS178D4, PS185L2, PS197P3, PS242B6, PS242G4, PS242H10, PS242K17, PS244A2, and PS244D1.

A further aspect of the subject invention is the discovery of new pesticidal activities for known *B.t.* isolates and toxins. Specifically exemplified herein is the discovery that *B.t.* isolates PS86Q3 and PS201T6, and toxins therefrom, can be used for the control of nematodes. In a preferred embodiment, the product of the 86Q3a gene, and fragment thereof; are used to control nematode pests.

Toxins with activity against corn rootworm are also an aspect of the subject invention.

In a preferred embodiment, the genes described herein which encode pesticidal toxins are used to transform plants in order to confer pest resistance upon said plants. Such transformation of plants can be accomplished using techniques well known to those skilled in the an and would typically involve modification of the gene to optimize expression of the toxin in plants.

BRIEF DESCRIPTION OF THE SEQUENCES

SEQ ID NO. 1 is a nucleotide sequence designated V3, useful as a primer according to the subject invention.

SEQ ID NO. 2 is a nucleotide sequence designated V5, useful as a primer according to the subject invention.

SEQ ID NO. 3 is a nucleotide sequence designated V7, useful as a primer according to the subject invention.

SEQ ID NO. 4 is a nucleotide sequence designated ΔV5', useful as a primer according to the subject invention.

SEQ ID NO. 5 is a nucleotide sequence designated ΔV8', useful as a primer according to the subject invention.

SEQ ID NO. 6 is a 16S rRNA forward primer used according to the subject invention.

SEQ ID NO. 7 is a 16S rRNA reverse primer used according to the subject invention.

SEQ ID NO. 8 is the nucleotide sequence of toxin 167P according to the subject invention.

SEQ ID NO. 9 is the deduced amino acid sequence of toxin 167P.

DETAILED DISCLOSURE OF THE INVENTION

The subject invention concerns materials and methods for the control of pests. In specific embodiments, the subject invention pertains to new *Bacillus thuringiensis* isolates and toxins which have activity against nematodes. Certain of the toxins also have activity against coleopteran pests. The subject invention further concerns novel genes which encode these pesticidal toxins and novel methods for identifying and characterizing *B.t.* genes which encode toxins with useful properties.

In one embodiment, the subject invention concerns materials and methods including nucleotide primers and probes for isolating and identifying *Bacillus thuringiensis (B.t.)* genes encoding protein toxins which are active against nematode pests. The nucleotide sequences described herein can also be used to identify new pesticidal *B.t.* isolates. The invention further concerns the genes, isolates, and toxins identified using the methods and materials disclosed herein.

It is well known that DNA possesses a fundamental property called base complementary. In nature, DNA ordinarily exists in the form of pairs of anti-parallel strands, the bases on each strand projecting from that opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation", of the two strands. If the DNA is then placed in conditions which make hydrogen bonding of the bases thermodynamically favorable, the DNA strands will anneal, or "hybridize", and reform the original double stranded DNA. If carried out under appropriate conditions, this hybridization can be highly specific. That is, only strands with a high degree of base complementary will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al., 1985). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan. It is important to note that the mutational, insertional, and deletional variants generated from a given primer sequence may be more or less efficient than the original sequences. Notwithstanding such differences in efficiency, these variants are within the scope of the present invention.

In addition, PCR-amplified DNA may serve as a hybridization probe. In order to analyze *B.t.* DNA using the nucleotide sequences of the subject invention as probes, the DNA can first be obtained in its native, double-stranded form. A number of procedures are currently used to isolate DNA and are well known to those skilled in this art.

One approach for the use of the subject invention as probes entails first identifying by Southern blot analysis of a gene bank of the *B.t.* isolate all DNA segments homologous with the disclosed nucleotide sequences. Thus, it is possible, without the aid of biological analysis, to know in advance the probable activity of many new *B.t.* isolates, and of the individual endotoxin gene products expressed by a given *B.t.* isolate. Such a probe analysis provides a rapid method for identifying potentially commercially valuable insecticidal endotoxin genes within the multifarious subspecies of *B.t.*

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane in a manner that retains the geometry of the pieces. The membrane can then be dried and prehybfidized to equilibrate it for later immersion in a hybridization solution. The manner in which the nucleic acid is affixed to a solid support may vary. This fixing of the DNA for later processing has great value for the use of this technique in field studies, remote from laboratory facilities.

The particular hybridization technique is not essential to the subject invention. As improvements are made in hybridization techniques, they can be readily applied.

As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

The nucleotide segments of the subject invention which are used as probes can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. For synthetic probes, it may be most desirable to use enzymes such as polynucleotide kinase or terminal transferase to end-label the DNA for use as probes.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO93/16094. The probe may also be labeled at both ends with different types of labels for ease of separation, as, for example, by using an isotopic label at the end mentioned above and a biotin label at the other end.

The amount of labeled probe which is present in the hybridization solution will vary widely, depending upon the nature of the label, the amount of the labeled probe which can reasonably bind to the filter, and the stringency of the hybridization. Generally, substantial excesses of the probe will be employed to enhance the rate of binding of the probe to the fixed DNA.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under stringent conditions by techniques well known in the art, as described, for example, in Keller and Manak, 1987.

Duplex formation and stability depend on substantial complementarity between the two strands of a hybrid, and, as noted above, a certain degree of mismatch can be tolerated. Therefore, the nucleotide sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a nucleotide sequence of the present invention as a probe to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed nucleotide sequences can be readily prepared by methods which are well known to those skilled in the art. These variants can be used in the same manner as the instant probe sequences so long as the variants have substantial sequence homology with the probes. As used herein, substantial sequence homology, refers to homology which is sufficient to enable the variant to function in the same capacity as the original probe. Preferably, this homology, is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Preline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | Termination signal | TGA |

Key: Each 3-letter deoxynucleotide triplet corresponds to a trinucleotide of mMRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.
A = adenine
G = guanine
C = cytosine
T = thymine
X = T or C if Y is A or G
X = C if Y is C or T
Y = A, G, C or T if X is C
Y = A or G if X is T
W = C or A if Z is A or G
W - C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the amino acid sequence of *B.t.* toxins can be encoded by equivalent nucleotide sequences encoding the same amino acid sequence of the protein. Accordingly, the subject invention includes probes which would hybridize with various polynucleotide sequences which would all code for a given protein or variations of a given protein. In addition, it has been shown that proteins of identified structure and function may be constructed by changing the amino acid sequence if such changes do not alter the protein secondary structure (Kaiser, E. T., Kezdy, F. J. [1984] *Science* 223:249–255).

The sequences and lengths of five cryV-specific primers useful according to the subject invention are shown in Table 1.

TABLE 1

| Primer name | Sequence | length |
|---|---|---|
| V3 | GATCGTMTWGARTTTRTTCC (SEQ ID NO. 1) | 20-mer |
| V5 | AAAGTNGATGCMTTATCWGATGA (SEQ ID NO. 2) | 23-mer |
| V7 | ACACGTTATAHDGTTTCTGG (SEQ ID NO. 3) | 20-mer |
| ΔV5' | TCATCWGATAAKGCATCNAC (SEQ ID NO. 4) | 20-mer |
| ΔV8' | TGGACGDTCTTCAMKAATTTCYAAA (SEQ ID NO. 5) | 25-mer |

Following is a table which provides characteristics of certain isolates useful according to the subject invention.

TABLE 2

Description of B.t. strains toxic to nematodes

| Culture | Crystal Description | Approx. MW (kDa) | Serotype | NRRL Deposit | Deposit Date |
|---------|---------------------|------------------|----------|--------------|--------------|
| PS32B | attached amorphic, fibrous flat square | 86, 52, 26 | non-motile | B-21531 | 3-14-96 |
| PS49C | small dark sphere | 133, 62 | 3 | B-21532 | 3-14-96 |
| PS52E3 | amorphic round | 130, 127, 63 | 3 | B-21533 | 3-14-96 |
| PS54G2 | small bipyramid | 140, 128, 112, 95, 62, 45, 43, 41 | non-motile | B-21543 | 3-20-96 |
| PS101CC3 | attached long | 142, 135, 129 | N.D. | B-21534 | 3-14-96 |
| PS178D4 | attached amorphic, round-ovoid, non-refractile | 95, 85, 65 | non-motile | B-21544 | 3-20-96 |
| PS185L2 | attached multiple round amorphic, BP with ort, long thin | 150, 98, 45, 39 | 6, entomocidus | B-21535 | 3-14-96 |
| PS197P3 | amorphic, long thin dark, smaller round | 35 | non-motile | B-21536 | 3-14-96 |
| PS242B6 | multiple amorphic (many unlysed canoes) | 130, 65 | N.D. | B-21537 | 3-14-96 |
| PS242G4 | multiple amorphic | 130 | N.D. | B-21538 | 3-14-96 |
| PS242H10 | spherical and large attached amorphic | 30 | N.D. | B-21439 | 3-14-96 |
| PS242K17 | large attached multiple light amorphic | 55 | N.D. | B-21540 | 3-14-96 |
| PS244A2 | amorphic, spore-sized | 130, 60 | N.D. | B-21541 | 3-14-96 |
| PS244D1 | single large spherical, spore-sized with "nub" | 130 | N.D. | B-21542 | 3-14-96 |
| PS74G1 | amorphic | 145, 1215, 100, 90, 60 | 10, darmstadiensis | B-18397 | 8-16-88 |
| PS75J1 | attached amorphic | 86, 80, 74, 62 | non-motile | B-18781 | 3-7-91 |
| PS83E5 | multiple attached | 42, 37 | non-motile | B-18782 | 3-7-91 |
| PS86Q3 | attached long | 155, 135, 98, 62, 58 | novel | B-18765 | 2-6-91 |
| PS98A3 | attached long | 140, 130, 125 | 10, darmstadiensis | B-18401 | 8-16-88 |
| PS101Z2 | attached long | 142, 135, 128 | 10, darmstadiensis | B-18890 | 10-1-91 |
| PS158C2 | amorphic, flat irregular | 130, 47, 38, 33 | 4 | B-18872 | 8-27-91 |
| PS201T6 | amorphic, elliptical and bipyramid | 133, 31 | 24, neoleoensis | B-18750 | 9-1-91 |
| PS204C3 | attached multiple amorphic and ellipse | 100, 92, 47, 35 | non-motile | B-21008 | 6-10-92 |
| PS17 | amorphic, attached long | 140, 90, 60 | 10, darmstadiensis | B-18243 | 7-28-87 |
| PS33F2 | long bipyramid | 140, 115, 90, 60 | wuhanensis | B-18244 | 7-28-87 |
| PS63B | amoprhic | 84, 82, 78 | wuhanensis | B-18246 | 7-28-87 |
| PS52A1 | multiple attached | 58, 45 | wuhanensis | B-18245 | 7-28-87 |
| PS69D1 | elongated | 34, 38, 145 | non-motile | B-18247 | 7-28-87 |
| PS80JJ1 | multiple attached | 130, 90, 47, 37 | 4a4b, sotto | B-18679 | 7-17-90 |
| PS158D5 | attached amorphic | 80 | novel | B-18680 | 7-17-90 |
| PS167P | attached amorphic | 120 | novel | B-18681 | 7-17-90 |
| PS169E | attached amorphic | 150, 128, 33 | non-motile | B-18682 | 7-17-90 |
| PS177F1 | multiple attached | 140, 116, 103, 62 | non-motile | B-18683 | 7-17-90 |
| PS177G | multiple attached | 135, 125, 107, 98, 62 | non-motile | B-18684 | 7-17-90 |
| PS204G4 | multiple attached | 105, 98, 90, 60, 44, 37 | non-motile | B-18685 | 7-17-90 |
| PS204G6 | long amorphic | 23, 21 | wuhanensis | B-18686 | 7-17-90 |

N.D. = not determined

As noted in Table 2, certain B.t. isolates useful according to the subject invention are available from the permanent collection of the Agricultural Research Service Patent Culture Collection (NRRL), Northern Regional Research Center, 1815 North University Street, Peoria, Ill. 61604, USA.

Cultures which have been deposited for the purposes of this patent application were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

Control of nematodes, or coleopterans, using the isolates, toxins, and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention. Recombinant microbes may be, for example, a B.t., E. coli, or Pseudomonas. Transformations can be made by those skilled in the art using standard techniques. Materials necessary for these transformations are disclosed herein or are otherwise readily available to the skilled artisan. For example, the gene encoding the 167P toxin is provided herein as SEQ ID NO. 8. The deduced amino acid sequence for the 167P toxin is, provided in SEQ ID NO. 9. A description of the PS167P isolate can be found in WO94/16079, which also provides a description of the cloning of the 80JJ1 gene. The nematicidal toxin known as 86Q3(a) found in PS8603 is encoded by a gene described in WO92/20802. Similarly, U.S. Pat. No. 5,488,432 describes the 201T6 gene which can be used to encode nematicidal toxins according to the subject invention. Also, *B.t.* isolates harboring genes encoding pesticidal toxins have been deposited as described herein.

Following are examples which illustrate procedures for practicing the invention. These examples should not be construed as limiting. All percentages are by weight and all solvent mixture proportions are by volume unless otherwise noted.

Example 1-Culturing of *B.t.* Isolates Useful According to the Invention

A subculture of *B.t.* isolates, or routants thereof, can be used to inoculate the following peptone, glucose, salts medium:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$Solution (100 ml) | 3.66 g |
| $CaCl_2.2H_2O$ | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

Example 2-Nematode Bioassay

C. elegans eggs were purified from gravid adult hermaphrodites, followed by hatching, feeding *B.t.*-based materials to a population of L1 or L2 larvae, followed by a 3-day bioassay time. Hatched L1 larvae remain viable at 15° C. for more than two weeks and neither grow nor die in the absence of a bacterial food source. C. elegans adapt rapidly to a diet of non-toxic *B.t.* spores (and crystals), although they grow more slowly than on their usual bacterial food source, *E. coli.*

This bioassay was validated by feeding approximately 100 L1 or L2 C. elegans larvae in 300 82 l bioassay volume in 24-well microliter trays with 4 doses (1, 5, 10, or 25 µl of washed biomass) of the following bacterial cells:

| | |
|---|---|
| *B.t.* PS17 | known nematicidal isolate |
| *B.t.* PS80JJ1 | known nematicidal isolate |
| *B.t.* PS167P | known nematicidal isolate |
| *B.t.* HD-73 | negative control strain |
| *E. coli* strain MC1061 | normal *C. elegans* food source |
| No bacteria | |

All nematodes were dead after 3 days at room temperature when incubated with the three nematicidal isolates, but proceeded to their full-grown adult stage with HD-73 or MC1061. After 5 days, L2 progeny were observed along with fully-grown adults on high doses of MC1061; HD-73 yielded only fully grown adults during this time.

Thus, all 3 known nematicidal isolates killed all nematodes, even at the lowest rate tested, while the non-toxic *B.t.* strain permitted full population growth without progeny interference even at the highest rate tested.

Example 3-Isolation and Preparation of Cellular DNA for PCR

DNA can be prepared from cells grown on Spizizen's agar, or other minimal agar known to those skilled in the art, for approximately 16 hours. Spizizen's casamino acid agar comprises 23.2 g/l Spizizen's minimal salts [$(NH_4)_2SO_4$, 120 g; $K_2HPO_4$, 840 g; $KH_2PO_4$, 360 g; sodium citrate, 60 g; $MgSO_4$. $7H_2O$, 12 g. Total: 1392 g]; 1.0 g/l vitamin-free casamino acids; 15.0 g/l Difco agar. In preparing the agar, the mixture was autoclaved for 30 minutes, then a sterile, 50% glucose solution can be added to a final concentration of 0.5% (1/100 vol). Once the cells are grown for about 16 hours, an approximately 1 $cm^2$ patch of cells can be scraped from the agar into 300/µl of 10 mM Tris-HC1 (pH 8.0)-1 mM EDTA. Proteinase K was added to 50 µg/ml and incubated at 55° C. for 15 minutes. Other suitable proteases lacking nuclease activity can be used. The samples were then placed in a boiling water bath for 15 minutes to inactivate the proteinase and denature the DNA. This also precipitates unwanted components. The samples are then centrifuged at 14,000 ×g in an Eppendorf microfuge at room temperature for 5 minutes to remove cellular debris. The supernatants containing crude DNA were transferred to fresh tubes and frozen at −20° C. until used in PCR reactions.

Example 4-PCR Amplification

Conditions for multiplex PCR amplification were:

TABLE 3

PCR amplification conditions

| Reagent | Final reaction concentration |
|---|---|
| Taq buffer | 1x |
| $MgCl_2$ | 2.0 mM |
| dNTPs | 0.1 mM |
| rRNA primers (forward & reverse) | 0.05 pmol/µl each |
| cryV-specific primers (forward & reverse) | 0.20 pmol/µl each |
| crude total *B.t. DNA*[1] | 15 µl |

[1]Total reaction volume: 49.5 µl.

Samples were preheated to 94° C. for 3 minutes, then quick chilled on ice. 0.5 µl Taq polymerase (5 units/ml) was added and overlaid with 50 µlight mineral oil. Cycle conditions were: {94° C., 1 minute; 42° C., 2 minutes; 72° C., 3 minutes +5 second/cycle}, repeated for 30 cycles, and held at 4° C. or −20° C. until gel analysis.

Internal positive controls for each PCR reaction in the screen were included: forward and reverse 16S rRNA gene primers, yielding a PCR-amplified fragment of 182 bp corresponding to nucleotide positions 1188 to 1370 in the sequence (Ash, C. et al. [1991] *Lett. Appl. Microbiol.* 13:202–206). This size is smaller than fragments expected from any of the cryV-specific primer pairs. The two rRNA primers were:

TABLE 4

| Primer name | Sequence | length |
|---|---|---|
| rRNAfor | CCGGAGGAAGGTGGGGATG (SEQ ID NO. 6) | 19-mer |
| rRNArev | CGATTACTAGCGATTCC (SEQ ID NO. 7) | 17-mer |

TABLE 5

PCR amplification of nematode-active B.t. strains

| | | | Expected size (bp) using primer pair | | | |
|---|---|---|---|---|---|---|
| Strain | Gene | Gene name | V3-ΔV5' | V3-ΔV8' | V7-ΔV8' | V5-ΔV8' |
| PS17 | 17a | cryVAa | 817 | 1379 | 317 | 582 |
| PS17 | 17b | cryVAb | 526 | 1088 | 317 | 582 |
| PS17 | 86Q3c-like | cryVAc | 337 | 899 | 317 | 582 |
| PS86Q3 | 86Q3a | cryVD | 562 | 1124 | 317 | 582 |
| PS86Q3 | 86Q3c | cryVAc | 337 | 899 | 317 | 582 |
| PS33F2 | 33F2 | cryVB | 547 | 1112 | 320 | 585 |
| PS80JJ1 | 80JJ1 | cryVE | 289 | 860 | 323 | 591 |
| PS167P | 167P | 167P | 196 | 800 | 332 | 599 |

Example 5-Cloning of Novel Pesticidal Genes Using Oligonucleotide Primers

Nematicidal toxin genes of new B.t. strains can be obtained from their DNA by performing the standard polymerase chain reaction procedure as in Example 4 using the oligonucleotides of SEQ ID NO. 4 or SEQ ID NO. 5 as reverse primers and SEQ ID NO. 1, SEQ ID NO. 2, or SEQ ID NO. 3 as forward primers. The expected PCR fragments are approximately 200 to 1000 bp with reverse primer SEQ ID NO. 4 and forward primer SEQ ID NO. 1. Fragments of about 300 to about 1500 bp are expected using the reverse primer SEQ ID NO. 5 and the forward primer SEQ ID NO. 1. The expected PCR fragments are approximately 400 to 800 bp using SEQ ID NO. 5 as reverse a primer, with SEQ ID NO. 2 as a forward primer. Fragments of approximately 200 to 650 bp are expected using the reverse primer SEQ ID NO. 5 and the forward primer SEQ ID NO. 3. Amplified DNA fragments of the indicated sizes can be radiolabeled and used as probes to clone the entire endotoxin gene.

Example 6-Screening of B.t. Isolates for Genes Encoding Nematode- and Coleopteran-Active Toxins A large number of B.t. strains were screened by PCR as described above. Certain of these strains were identified as "cryV positive". In a preferred embodiment, "cryV positive" refers to strains for which PCR amplification using the primer pair V7-ΔV8'(SEQ ID NOS. 3 and 5) yields a fragment of about 315 to about 325 bp. Most preferably, this fragment is about 320 bp. Approximate sizes of base pair fragments produced from those eleven strains were as follows:

TABLE 6

PCR amplification of DNA from miscellaneous B.t. strains

| | Approximate size (bp) using primer pair | | | |
|---|---|---|---|---|
| Strain | V3-ΔV5' | V3-ΔV8' | V7-ΔV8'* | V5-ΔV8' |
| PS54G2 | 470, 530 | 950, 590 | 320 (+) | 585 |
| PS62B1 | 600, 540, 480 | 990, 590, 470 | 320 (+) | 585 |
| PS72N | 560 | 600, 540 | 850 (u) | n.d. |
| PS74G1 | 530 | 880, 590, 470 | 320 (+) | 585 |
| PS75G2 | 560 | n.d. | 800 (u) | n.d. |
| PS86E | 560 | 600, 540 | 800 (u) | n.d. |
| PS88F11 | 560 | n.d. | 1000 (u) | n.d. |
| PS98A3 | 530, 390 | 900 | 320 (+) | 585 |
| PS177F1 | 860, 530, 390 | 880, 590, 470 | 320 (+) | 585 |
| PS177G | 530 | n.d. | 320 (+) | 585 |
| PS212 | 620, 530, 470 | 950, 590, 470 | 320 (+) | 585 | n.d. = not determined
*symbols in parentheses indicate whether the strain was "cryV positive" (+) or "cryV unusual" (u).

Example 7-Bioassay Results

Bioassays for nematode activity were performed as described in Example 3. PCR using the V7-ΔV8' primer pair was performed as described herein for many of the isolates which were bioassayed. The isolates were considered cryV PCR-positive if PCR using the V7-ΔV8' primer pair yielded an approximately 320-bp fragment. If PCR with this primer pair yielded fragments of other sizes, then the isolate was designated "unusual". If no fragment was produced, then the isolate was designated as "negative". The results of these bioassays and the PCR experiment are shown in Table 7. Nematode activity was found to be very highly correlated with a "positive cryV" PCR profile. It should be noted that a negative or unusual cryV PCR profile does not preclude nematode activity. This is because there are nematicidal toxins other than cryV toxins which could still provide activity against nematodes.

TABLE 7

Summary of C. elegans bioassay results

| Strain/clone | cryV PCR | C.e. toxicity |
|---|---|---|
| E. coli MC1061 | N.D. | – |
| HD-73 | negative | – |
| PS17 | positive | + |
| PS33F2 | positive | + |
| PS63B | N.D. | + |
| PS69D1 | N.D. | + |
| PS86A1 | N.D. | + |
| PS158D5 | negative | + |
| PS169E | negative | + |
| PS177F1 | positive | + |
| PS177G | positive | + |
| PS204G4 | N.D. | + |
| PS204G6 | N.D. | + |
| PS80JJ1 | positive | + |
| PS167P | positive | + |
| PS54G2 | positive | + |
| PS62B1 | positive | – |
| PS72N | unusual | – |
| PS74G1 | positive | + |
| PS75G2 | unusual | – |
| PS86E | unusual | – |
| PS88F11 | unusual | – |
| PS98A3 | positive | + |
| PS212 | positive | – |
| PS86Q3 | positive | + |
| PS242B6 | N.D. | +/– |
| PS242G4 | N.D. | +/– |
| PS242H10 | N.D. | + |
| PS242K17 | N.D. | + |
| PS244A2 | N.D. | +/– |
| PS244D1 | N.D. | +/– |
| PS32B1 | N.D. | + |
| PS49C | neative | + |
| PS52E3 | negative | + |
| PS75J | negative | + |
| PS83E5 | N.D. | + |
| PS101CC3 | N.D. | + |
| PS101Z2 | N.D. | + |
| PS158C2 | N.D. | +/– |
| PS178D4 | N.D. | + |
| PS185L2 | negative | + |
| PS197P3 | N.D. | +/– |
| PS201T6 | N.D. | +/– |
| PS204C3 | N.D. | + |

+ = acute toxicity
+/– = stunting of larvae
– = little or no activity
N.D. = not determined Recombinant hosts expressing specific toxins were constructed and tested in bioassays, as described above, to evaluate nematicidal activity. The results from these assays are shown in Table 8.

TABLE 8

Description of clones toxic to nematodes

| Clone | Host* | Toxin expressed | Parent strain | Toxin mol. wt. (kDa) | C. elegans activity |
|---|---|---|---|---|---|
| MR515 | B.t. | CryVD/Cry5B | PS86Q3 | 140 | + |
| MR871 | P.f. | CryVD/Cry5B | PS86Q3 | 140 | + |
| MR531 | B.t. | unnamed | PS167P | 132 | + |
| MR506 | B.t. | CryVIA/Cr6A | PS86A1 | 54 | + |
| MR508 | B.t. | CryVB/Cry12A | PS33F2 | 142 | +/– |
| cryB | B.t. | none | — | — | — |
| MR839 | P.f. | none | — | — | — |

B.t. = Bacillus thuringiensis
P.f. = Pseudomonas fluorescens

Example 8-Insertion of Toxin Genes into Plants

One aspect of the subject invention is the transformation of plants with genes encoding a toxin active against coleopteran and/or nematode pests. The transformed plants are resistant to attack by coleopterans and/or nematodes.

Genes encoding pesticidal toxins, as disclosed herein, can be modified for optimum expression in plant, linked to a plant selectable marker gene, and inserted into a genome of plant cell using a variety of techniques which are well known to those skilled in the art. Any plant may be used in accordance with this invention, including angiosperms, gymnosperms, monocotyledons and dicotyledons. Preferred plants include soybean, sunflower, cotton, potato, alfalfa, maize, rice and wheat. The transformation method itself is not critical to the invention but may include transformation with T-DNA using *Agrobacterium tumefaciens* or *A. rhizogenes* as the transformation agent, liposome fusion, microinjection, microprojectile bombardment, chemical agent (PEG or calcium chloride)-assisted DNA uptake, or electroporation, as well as other possible methods. Reference may be made to the literature for full details of the known methods, especially Holsters et al., 1978; Fromm et al., 1985; Horsch et al., 1985; Herrera-Estrella et al., 1983; Crossway et al., 1986; Lin, 1966; and Steinkiss and Stabel, 1983.

Use of a plant selectable marker in transformation allows for selection of transformed cells rather than cells that do not contain the inserted DNA. Various markers exist for use in plant cells and generally provide resistance to a biocide or antibiotic, including but not limited to, kanamycin, G418, hygromycin, and phosphinothricin. Visual markers including but not limited to b-glucuronidase, b-galactosidase, B-peru protein, green fluorescent protein, and luciferase may also be used. After transformation, those cells that have the DNA insert can be selected for by growth in a defined medium and assayed for marker expression, whether by resistance or visualization. Cells containing the DNA insert can be regenerated into plants. As long as stably transformed plants are obtained, the method used for regeneration will depend on the plant tissue and transformation method used and is not critical to the invention. However, for example, where cell suspensions have been used for transformation, transformed cells can be induced to produce calli and the calli subsequently induced to form shoots, which may then be transferred to an appropriate nutrient medium to regenerate plants. Alternatively, explants such as hypocotyl tissue or embryos may be transformed and regenerated by shoot induction in the appropriate media, followed by root and whole plant formation. Whatever regeneration method is used, the result will be stably transformed plants that can vegetatively and sexually transmit the transformed trait(s) to progeny, so that, if necessary, the transformed plant can be crossed with untransformed plants in order to transfer the trait to more appropriate germplasm for breeding purposes.

It should be understood that the examples and embodiments described herein are for illustrative purposes only and that various modifications or changes in light thereof will be suggested to persons skilled in the art and are to be included within the spirit and purview of this application and the scope of the appended claims.

References

U.S. patents

U.S. Pat. No. 4,448,885.
U.S. Pat. No. 4,467,036.
U.S. Pat. No. 4,683,195.
U.S. Pat. No. 4,683,202.
U.S. Pat. No. 4,797,276.
U.S. Pat. No. 4,800,159.
U.S. Pat. No. 4,853,331.
U.S. Pat. No. 4,817,006.
U.S. Pat. No. 4,948,734.
U.S. Pat. No. 4,990,332
U.S. Pat. No. 5,039,523.
U.S. Pat. No. 5,093,120.
U.S. Pat. No. 5,126,133.
U.S. Pat. No. 5,151,363.
U.S. Pat. No. 5,164,180.
U.S. Pat. No. 5,169,629.
U.S. Pat. No. 5,204,237
U.S. Pat. No. 5,236,843.
U.S. Pat. No. 5,262,399.
U.S. Pat. No. 5,270,448.
U.S. Pat. No. 5,281,530.
U.S. Pat. No. 5,322,932.
U.S. Pat. No. 5,350,577.
U.S. Pat. No. 5,426,049.
U.S. Pat. No. 5,439,881.
U.S. Pat. No. 5,488,432.

Foreign Patent Documents

EP 0 409 438.
EP 0 626 809.
WO92/20802.
WO93/16094.
WO94/16079.

Other References

Ash, C. et al. (1991) *Lett. Appl. Microbiol.* 13:202–206.

Beegle, C. C., (1978) "Use of Entomogenous Bacteria in Agroecosystems", *Developments in Industrial Microbiology* 20:97–104.

Bottjer, Bone and Gill (1985) Experimental Parasitology 60:239–244.

Carozzi, N. B., V. C. Kramer, G. W. Warren, S. Evola, G. Koziel (1991) *Appl. Env. Microbid.* 57(11):3057–3061.

Ciordia, H., W. E. Bizzell (1961) *Jour. of Parasitology* 47:41 (abstract).

Coles, G. C. (1986) "Anthelmintic resistance in sheep", In *Veterinary Clinics of North America: Food Animal Practice*, Vol 2:423–432 (Herd, R. P., Ed.) W. B. Saunders, N.Y.

Couch, T. L. (1980) "Mosquito Pathogenicity of *Bacillus thuringiensis* vat. *israelensis*", *Developments in Industrial Microbiology* 22:61"76.

Crossway et al (1986) *Biotechniques* 4:320–334.

Feitelson, J. S., J. Payne, L. Kim (1992) *Bio/Technology* 10:271–275.

Fromm et al. (1985) PNAS 82:5824–5828.

Gaertner, F. H. (1989) "Cellular Delivery Systems for Insecticidal Proteins: Living and Non-Living Microorganisms", in *Controlled Delivery of Crop Protection Agents*, R. M. Wilkins, ed., Taylor and Francis, New York and London, 1990, pp. 245–255.

Gaertner, F. H., L. Kim (1988) *TIBTECH* 6:S4–S7.

Herrera-Estrella et al. (1983) *Nature* 303:209–313.

Höfte, H., H. R. Whiteley (1989) *Microbiological Reviews* 52(2):242–255.

Holsters et al (1978) *Mol. Gen. Genet.* 163:181–187.

Horsch et al. (1978) *Science* 228:1229–1231.

Ignoffo, C. M., Dropkin, V. H. (1977) *J. Kans. Entomol. Soc.* 50:394–398.

Kaiser, E. T., Kezdy, F. J. [1984] *Science* 223:249–255).

Keller, G. H., M. M. Manak (1987) DNA Probes, Stockton Press, New York, NY, pp. 169–170.

Krieg, A., A. M. Huger, G. A. Langenbruch, W. Schnetter (1983) *Z. ang. Ent.* 96:500–508.

Lin (1966) *Science* 151:333–337.

Metcalf, R. L. (1986) in *Methods for the Study of Pest Diabrotica*, Drysan, J. L. and T. A. Miller (Eds.), Springer-Verlag, New York, N.Y., pp. vii–xv.

Prichard, R. K. et al. (1980) "The problem of anthelmintic resistance in nematodes", *Austr. Vet. J.* 56:239–251.

Schnepf, H. E., H. R. Whiteley (1981) *Proc. Natl. Acad. Sci. USA* 78:2893–2897.

Saiki, Randall K., Stephen Sehaff, Fred Faloona, Kary B. Mullis, Glenn T. Horn, Henry A. Erlich, Norman Arnheim (1985) "Enzymatic Amplification of β-Globin Genomic Sequences and Restriction Site Analysis for Diagnosis of Sickle Cell Anemia", *Science* 230:1350–1354.

Steinkiss and Stable (1983) Protoplasma 116:222–227.

---

I claim:

1. A novel *Bacillus thuringiensis* isolate selected from the group consisting of PS32B (NRRL B-21531), PS 49C (NRRL B-21532), PSS52E3 (NRRL B-21533), PS54G2 (NRRL B-21543), PS101CC3 (NRRL B 21534), PS178D4 (NRRL B-21544), PS185L2 (NRRL B-21535), PS197P3 (NRRL B-21536), PS242B6 (NRRL B-21537), PS242G4 (NRRL B-21538), PS242H10 (NRRL B-21539), PS242K17 (NRRL B-21540), PS244A2 (NRRL B-21541), PS244D1 (NRRL B-21542).

2. An isolated polynucleotide sequence which encodes a nematicidal toxin from a *Bacillus thuringiensis* isolate selected from the group consisting of PS32B, PS49C, PS53E3, PS54G2, PS101CC3, PS178D4, PS185L2, PS197P3, PS242B6, PS242G4, PS242H10, PS242K17, PS244A2, and PS244D1.

3. The isolated polynucleotide sequence, according to claim 2, which encodes a nematicidal toxin from isolate PS32B.

4. The isolated polynucleotide sequence, according to claim 2, which encodes a nematicidal toxin from isolate PS49C.

5. The isolated polynucleotide sequence, according to claim 2, which encodes a nematicidal toxin from isolate PS52E3.

6. The isolated polynucleotide sequence, according to claim 2, which encodes a nematicidal toxin from isolate PS54G2.

7. The isolated polynucleotide sequence, according to claim 2, which encodes a nematicidal toxin from isolate PS101CC3.

8. The isolated polynucleotide sequence, according to claim 2, which encodes a nematicidal toxin from isolate PS178D4.

9. The isolated polynucleotide sequence, according to claim 2, which encodes a nematicidal toxin from isolate PS185L2.

10. The isolated polynucleotide sequence, according to claim 2, which encodes a nematicidal toxin from isolate PS197P3.

11. The isolated polynucleotide sequence, according to claim 2, which encodes a nematicidal toxin from isolate PS242B6.

12. The isolated polynucleotide sequence, according to claim 2, which encodes a nematicidal toxin from isolate PS242G4.

13. The isolated polynucleotide sequence, according to claim 2, which encodes a nematicidal toxin from isolate PS242H10.

14. The isolated polynucleotide sequence, according to claim 2, which encodes a nematicidal toxin from isolate PS242K17.

15. The isolated polynucleotide sequence, according to claim 2, which encodes a nematicidal toxin from isolate PS244A2.

16. The isolated polynucleotide sequence, according to claim 2, which encodes a nematicidal toxin from isolate PS244D1.

17. The isolated polynucleotide sequence of claim 2 which encodes a nematicidal toxin, wherein said polynucleotide sequence can be amplified by PCR using a primer pair selected from the group consisting of:

(a) the V3–ΔV5' primer pair, SEQ ID NO. 1 and SEQ ID NO. 4;

(b) the V3–ΔV8' primer pair, SEQ ID NO. 1 and SEQ ID NO. 5;

(c) the V7–ΔV8' primer pair, SEQ ID NO. 3 and SEQ ID NO. 5; and (d) the V5–ΔV8' primer pair, SEQ ID NO. 2 and SEQ ID NO. 5.

18. The isolated polynucleotide sequence, according to claim 17, wherein said polynucleotide sequence can be amplified with the V7–ΔVS' primer pair, SEQ ID NO. 3 and SEQ ID NO. 5.

19. The isolated polynucleotide sequence, according to claim 18, wherein said amplification produces a fragment of about 320 bp.

20. A recombinant host transformed with a polynucleotide sequence of claim 17.

21. The recombinant host, according to claim 20 wherein said recombinant host is a bacterium.

22. The recombinant host, according to claim 21, wherein said bacterium is selected from the group consisting of *Bacillus thuringiensis*, *Escherichia coli*, and *Pseudomonas*.

23. An isolated polynucleotide sequence which is SEQ ID NO. 4.

* * * * *

UNITED STATES PATENT AND TRADEMARK OFFICE
CERTIFICATE OF CORRECTION

PATENT NO. : 5,670,365

DATED : September 23, 1997

INVENTOR(S) : Jerald S. Feitelson

It is certified that error appears in the above-identified patent and that said Letters Patent is hereby corrected as shown below:

Column 3, line 34: "GATCGTMTWGARTTRTTCC" should read

--GATCGTMTWGARTTTRTTCC--;

line 40: "ACACGTATAHDGTTTFCTGG" should read

--ACACGTATAHDGTTTCTGG--.

Column 4, line 20-21: "and fragment thereof; " should read --and fragments thereof,--;

line 28: "in the an" should read --in the art--;

line 55: "*thuringiensis*isolates" should read --*thuringiensis* isolates--.

Column 5, line 4: "complementary." should read --complementarity.--;

line 22: "complementary" should read --complementarity--.

Column 8, line 17: "Preline (Pro)" should read --Proline (Pro)--;

line 23: "mMRNA," should read --mRNA,--.

UNITED STATES PATENT AND TRADEMARK OFFICE
CERTIFICATE OF CORRECTION

PATENT NO.   : 5,670,365

DATED        : September 23, 1997

INVENTOR(S)  : Jerald S. Feitelson

It is certified that error appears in the above-identified patent and that said Letters Patent is hereby corrected as shown below:

Cols. 9&10, Table 2 (line 15, 3rd Col.): "145, 1215, 100, 90, 60" should read --145, 125, 100, 90, 60--;

Table 2 (line 28, 3rd Col.): "34, 38, 145" should read --34, 48, 145--

Column 10, line 65: "PS8603" should read --PS86Q3--.

Column 11, line 12: "routants" should read --mutants--;

line 55: "300 82 1 bioassay" should read --300 $\mu$l bioassay--;

line 56: "microliter" should read --microtiter--.

Column 12, line 24: "300/$\mu$l" should read --300 $\mu$l--;

line 56: "50 $\mu$light" should read --50 $\mu$l light--.

Col. 13, line 1, Table 4: "Table 4" should read --Table 4. Internal positive controls--.

Col. 15, Table 8, 4th row, 3rd col.: "CryVIA/Cr6A" should read --CryVIA/Cry6--.

Col. 17, Reference Sect., 8th listed patent: "U.S. Pat. No. 4,817,006" should read --U.S. Pat. No. 4,918,006--.

UNITED STATES PATENT AND TRADEMARK OFFICE
CERTIFICATE OF CORRECTION

Page 3 of 3

PATENT NO. : 5,670,365

DATED : September 23, 1997

INVENTOR(S) : Jerald S. Feitelson

It is certified that error appears in the above-identified patent and that said Letters Patent is hereby corrected as shown below:

Column 17, line 44: "*Microbid.*" should read --*Microbiol.*--.

Column 18, line 5: "vat." should read --var.--;

line 6: "22:61"76." should read --22:61-76.--;

line 41: "Sehaff" should read --Scharf--.

Column 31, line 7, Claim 10: "polynueleotide" should read --polynucleotide--.

Column 32, line 14, Claim 18: "V7–ΔVS'" should read --V7–ΔV8'--.

Signed and Sealed this

Twenty-seventh Day of January, 1998

*Attest:*

BRUCE LEHMAN

*Attesting Officer*      *Commissioner of Patents and Trademarks*